(12) United States Patent
Fornaro et al.

(10) Patent No.: US 8,753,632 B2
(45) Date of Patent: Jun. 17, 2014

(54) ANTIBODIES TO MODIFIED HUMAN IGF-1/E PEPTIDES

(75) Inventors: Mara Fornaro, Basel (CH); John Xu, Shanghai (CN); Yuan Gao, Shanghai (CN); Rainer Hillenbrand, Basel (CH); Francois Legay, Basel (CH); Daniela Stoellner, Basel (CH)

(73) Assignee: Novartis AG, Basel (CH)

( * ) Notice: Subject to any disclaimer, the term of this patent is extended or adjusted under 35 U.S.C. 154(b) by 347 days.

(21) Appl. No.: 13/128,335

(22) PCT Filed: Nov. 10, 2009

(86) PCT No.: PCT/EP2009/064947
§ 371 (c)(1),
(2), (4) Date: May 9, 2011

(87) PCT Pub. No.: WO2010/052344
PCT Pub. Date: May 14, 2010

(65) Prior Publication Data
US 2011/0218145 A1  Sep. 8, 2011

Related U.S. Application Data

(60) Provisional application No. 61/112,957, filed on Nov. 10, 2008.

(51) Int. Cl.
*A61K 39/395* (2006.01)
*C12N 5/12* (2006.01)
*C12N 15/00* (2006.01)
*C07K 16/22* (2006.01)

(52) U.S. Cl.
USPC ............. 424/141.1; 435/70.21; 435/326; 435/335; 530/388.1; 530/387.9; 530/388.23; 424/139.1; 424/145.1; 424/158.1

(58) Field of Classification Search
USPC ........................ 435/331; 530/387.9
See application file for complete search history.

(56) References Cited

U.S. PATENT DOCUMENTS

| 5,866,688 A | 2/1999 | Kim et al. |
| 6,924,361 B1 | 8/2005 | Laudano et al. |
| 2013/0059779 A1* | 3/2013 | Glass et al. ............. 514/8.6 |

FOREIGN PATENT DOCUMENTS

| WO | 2006/066912 A2 | 6/2006 |
| WO | 2007070432 A2 | 6/2007 |
| WO | 2007141309 A2 | 12/2007 |
| WO | WO 2007/141309 | * 12/2007 |
| WO | WO 2007/146689 A2 | 12/2007 |
| WO | 2010066868 A2 | 6/2010 |

OTHER PUBLICATIONS

Campbell, A. Laboratory Techniques in Biochemistry and Molecular Biology, vol. 13, Chapter 1, pp. 1-33 (1984).*
Edwards, Robert J. et al., "Targeting Antipeptide Antibodies Toward Cytochrom P450 Enzymes", Methods in Molecular Biology, Jan. 1, 2006, pp. 173-182, vol. 320, Humana Press Inc., NJ, US.
Sattayasai, N. et al., "Production of Subtype-Specific Antipeptide Antibodies to Human Interferon-.Alpha.1 and . Alpha.4", Journal of Interferon Research, Jun. 1, 1988, pp. 325-332, vol. 8, No. 3, Mary Ann Liebert, Inc., New York, NY, US.
Murayama et al., "A Novel Monoclonal Antibody Specific for the Amino-Truncated Beta-Amyloid Abeta5-40/42 Produced from Caspase-Cleaved Amyloid Precursor Protein", Journal of Neuroscience Methods, Mar. 27, 2007, pp. 244-249, vol. 161, No. 2, Elsevier Science Publisher B.V., Amsterdam, NL.
Nakamura, A. et al., "Anti-Peptide Antibodies to the P45O20 Subfamily in Rat, Dog and Man", Xenobiotica, Jan. 1, 1995, vol. 25, No. 10,, Taylor and Francis, London, GB.
Griffin H.M. et al., "A Human Monoclonal Antibody Specific for the Leucine-33" Blood, vol. 86, No. 12, pp. 4430-4436, (1985).
Campbell, A., "General Properties and Applications of Monoclonal Antibodies", Laboratory Techniques in Biochemistry and Molecular Biology, vol. 13, Chapter 1, pp. 1-32, (1984).

* cited by examiner

*Primary Examiner* — Elizabeth C Kemmerer
*Assistant Examiner* — Regina M Deberry
(74) *Attorney, Agent, or Firm* — Frank Wu

(57) ABSTRACT

High-specificity antibodies can distinguish between modified (e.g, hIGF-1/Ea 3mut) and endogenous wild-type human IGF-1 proteins. These antibodies have little or no cross-reactivity with hIGF-1 or hIGF-2. They also have little or no cross-reactivity with rodent IGF-1 or IGF-2. The antibodies can be used in pharmacokinetic (PK)/pharamcodynamic (PD) assessments of IGF-1/E peptides that have been administered to humans or animals. A sandwich ELISA assay, using the antibody of the invention as a capture antibody, can quantify the mutant IGF-1/E proteins in samples.

3 Claims, 5 Drawing Sheets

```
hIGF-1       1  ---GPETLCGAELVDALQFVCGDRGFYFNKPTGYGSSSRRAPQTGIVDECCFRSCDLRRL  57
hIGF-1/E wt  1  ---GPETLCGAELVDALQFVCGDRGFYFNKPTGYGSSSRRAPQTGIVDECCFRSCDLRRL  57
hIGF-1/E 3mut 1 ----GP-TLCGAELVDALQFVCGDRGFYFNKPTGYGSSSRAAPQTGIVDECCFRSCDLRRL 56
hIGF-2E      1  AYRPSETLCGGELVDTLQFVCGDRGFYFSRPASRVSRR----SRGIVEECCFRSCDLALL  56 hIGF-1        58  EMYCAPLKPAKSA-----------------  70  (SEQ ID NO:8)
hIGF-1/Ea wt  58  EMYCAPLKPAKSARSVRAQRHTDMPKTQK   86  (SEQ ID NO:9)
hIGF-1/Ea 3mut 57 EMYCAPLKPAKSA--VRAQRHTDMPKTQK   83  (SEQ ID NO:10)
hIGF-2/Ea     57  ETYCA--TPAKSARDVSTPPTVLPDNFPR   83  (SEQ ID NO:11)
```

FIG. 1

ANTIBODIES TO MODIFIED HUMAN IGF-1/E PEPTIDES

This application is a U.S. National Phase filing of International Application Serial No. PCT/EP2009/064947 filed 10 Nov. 2009 and claims priority to U.S. Provisional Application Ser. No. 61/112,957 filed 10 Nov. 2008, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 28, 2013, is named PAT052787-US-PCT_SL.txt and is 6,328 bytes in size.

FIELD OF THE INVENTION

This invention relates generally to immunoglobulins, antibodies and fragments thereof. In particular, the invention relates to the preparation and use of antibodies that bind immunospecifically to modified human insulin-like growth factor 1 proteins.

BACKGROUND OF THE INVENTION

Insulin-like growth factor 1 (IGF-1, somatomedin) is a small single-chain protein that induces muscle hypertrophy and blocks skeletal muscle atrophy. IGF-1 is initially synthesized in the human body as an IGF-1/E precursor, where E is an extension peptide at the C-terminus of the mature IGF-1 protein. The mature IGF-1 is initially encoded by one of three known splice variant mRNAs. The open reading frame of each mRNA encodes a precursor protein containing the 70 amino acid IGF-1 moiety and a particular extension (E) peptide at the C-terminus, which can be Ea, Eb or Ec, depending on the particular IGF-1 mRNA. The C-terminus E peptide is later cleaved as IGF-1 matures.

Modified recombinant human IGF-1/E proteins have been constructed and described in published PCT patent application WO2007/146689. These modified IGF-1/E peptides have longer half-life, increased stability, reduced affinity to inhibitory insulin-like growth factor binding proteins (IGFBPs), and increased efficacy compared to wild type IGF-1. An exemplary modified human IGF-1/E protein is hIGF-1/Ea 3mut (see FIG. 1). The "3mut" designation refers to a hIGF-1-E-peptide precursor having the following three sets of modifications: (1) deletion of G1, P2, and E3; (2) mutation of Arg 37 to Ala (R37A); and (3) deletion of R71 and S72. These hIGF-1/E 3mut peptides are proposed as being potential new drug for the treatment of skeletal muscle atrophy.

However, assessing the pharmacokinetics (PK) and pharacodynamics (PD) for this drug candidate is difficult, because the wild type and modified hIGF-1/E peptides differ with each other in only one or two amino acids at three separate positions over the length of the entire peptide chains (FIG. 1). No commercially available antibody recognizes the hIGF-1/Ea 3mut peptides without also detecting the endogenous hIGF-1.

SUMMARY OF THE INVENTION

The invention provides high-specificity antibodies that distinguish between modified (e.g. hIGF-1/Ea 3mut) and endogenous human IGF-1 proteins. The antibodies of the invention have little or no cross-reactivity with hIGF-1 or hIGF-2. They also have little or no cross-reactivity with rodent IGF-1 or IGF-2. The antibodies are useful for pharmacokinetic (PK) and pharamcodynamic (PD) assessments of IGF-1/E peptides that have been administered to humans or animals.

In one embodiment, the antibody of the invention binds immunospecifically to the peptide GPTLCGAELV (SEQ ID NO:1), but does not bind immunospecifically to the peptide GPETLCGAELV (SEQ ID NO:2). In another embodiment, the antibody of the invention binds immunospecifically to the peptide PAKSAVRAQR (SEQ ID NO:6) but does not bind immunospecifically to the peptide PTKAARSIRAQR (SEQ ID NO:7).

The invention therefore provides the antibodies QC1, QC2, QQ2, QQ5 and QQ6.

The antibodies may be monoclonal or polyclonal. They may be produced by immunisation of a suitable mammal, such as a mouse, rabbit, goat, horse, camel or shark.

Further included, within the scope of the invention are hybridomas that produce the antibodies of the invention, nucleic acid sequences encoding said antibodies, vectors, for example expression vectors, comprising such a nucleic acid sequence, as well as cells transformed with such vectors.

The invention also provides the hybridomas (deposited with DSMZ, Inhoffenstr. 7B, D-38124 Braunschweig, Germany), which can be used to express the antibodies QC1, QC2, QQ2, QQ5 and QQ6, respectively.

The following material was deposited on 19 Nov. 2009:
Cell culture 6H6G11 (QQ5) DSM ACC3024
Cell culture 7B1H12 (QQ6) DSM ACC3025
Cell culture 8B7A2 (QC2) DSM ACC3026
Cell culture 2C10B7 (QQ2) DSM ACC3027
Cell culture 7B9C6 (QC1) DSM ACC3028

The invention also provides a bioanalytical assay for assessing the pharmacokinetic (PK)/pharmacodynamic (PD) relationship of modified recombinant human IGF-1/E peptides. In one embodiment, the assay is a radioimmunoassay (RIA) or an Enzyme-Linked ImmunoSorbent Assay (ELISA), such as a sandwich ELISA, assay to quantify the mutant IGF-1/E proteins in preclinical and clinical samples, in which an antibody of the invention is used as the immunosorbent agent (capture antibody). In the applications, the antibodies can be labelled with an analytically-detectable reagent such as a radioisotope, a fluorescent molecule or an enzyme.

In addition, the antibodies of the invention are used to purify large quantities of IGF-1/E 3mut peptides, for example by affinity chromatography. The antibodies of the invention are thus useful for the commercial-scale purification of a pharmaceutical to treat muscle atrophy.

In one embodiment, the antibody used in the methods described above is selected from the list consisting of QC1, QC2, QQ2, QQ5 and QQ6.

DETAILED DESCRIPTION OF THE INVENTION

Antibodies of the Invention

DEFINITIONS

The definitions of certain terms as used in this specification are provided below. Definitions of other terms may be found in the *Illustrated Dictionary of Immunology, 2nd Edition*, Cruse, J. M. and Lewis, R. E., eds. (CRC Press, Boca Raton, Fla., 1995).

The administration of an agent or drug to a subject or subject includes self-administration and the administration by another. It is also to be appreciated that the various modes of treatment or prevention of medical conditions as described are intended to mean "substantial", which includes total but also less than total treatment or prevention, and wherein some biologically or medically-relevant result is achieved.

The term "antibody" means a polypeptide comprising a framework region from an immunoglobulin gene or fragments thereof that specifically binds and recognizes an epitope, e.g., an epitope found on a modified IGF-1/E peptide but not on a wild type IGF, such as the epitopes of the Peptide A and Peptide C antigens, both described below. Use of the term antibody is meant to include whole antibodies, including single-chain whole antibodies, and antigen-binding fragments thereof. The term "antibody" includes antigen-binding antibody fragments, including single-chain antibodies, which can comprise the variable regions alone, or in combination, with all or part of the following polypeptide elements: hinge region, $CH_1$, $CH_2$, and $CH_3$ domains of an antibody molecule. Also included in the invention are any combinations of variable regions and hinge region, $CH_1$, $CH_2$, and $CH_3$ domains. Antibody-related molecules useful as binding agents of the invention include, e.g., but are not limited to, Fab, Fab' and $F(ab')_2$, Fd, single-chain Fvs (scFv), single-chain antibodies, disulphide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a $F(ab')_2$ fragment, a bivalent fragment comprising two Fab fragments linked by a disulphide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., Nature 341: 544-546, 1989), which consists of a $V_H$ domain; and (vi) an isolated complementarity determining region (CDR). The term "antibody" includes single domain antibodies, maxibodies, minibodies, intrabodies, diabodies, triabodies, tetrabodies, v-NAR and bis-scFv (see, e.g., Hollinger & Hudson, Nature Biotechnology, 23, 9, 1126-1136 (2005)). Once antibodies have been raised, they may be chimerised or humanised. For example, to create a chimeric antibody, the variable regions can be linked to human constant regions using methods known in the art (see e.g., U.S. Pat. No. 4,816,567 to Cabilly et al.). To create a humanized antibody, the CDR regions can be inserted into a human framework using methods known in the art. See e.g., U.S. Pat. No. 5,225,539 to Winter, and U.S. Pat. Nos. 5,530,101; 5,585,089; 5693762 and 6180370 to Queen et al. in an alternative to this antigen binding portions of antibodies can be grafted into scaffolds based on polypeptides such as Fibronectin type III (Fn3) (see U.S. Pat. No. 6,703,199, which describes fibronectin polypeptide monobodies). Antigen binding portions can be incorporated into single chain molecules comprising a pair of tandem Fv segments (VH-CH1-VH-CH1) which, together with complementary light chain polypeptides, form a pair of antigen binding regions (Zapata et al., Protein Eng. 8(10):1057-1062 (1995); and U.S. Pat. No. 5,641,870).

The term "biological sample" means sample material derived from or contacted by living cells. The term "biological sample" is intended to include tissues, cells and biological fluids isolated from a subject, as well as tissues, cells and fluids present within a subject.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "immunologically reactive conditions" means conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols. See, Harlow & Lane, Antibodies, A Laboratory Manual (Cold Spring Harbor Publications, New York, 1988) for a description of immunoassay formats and conditions.

The term "immunospecifically" as used herein refers to the ability of an individual antibody combining site to react with only one antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody. As used herein, the term "high affinity" for an IgG antibody refers to an antibody having a KD of $10^{-8}$ M or less, $10^{-9}$ M or less, or $10^{-10}$ M, or $10^{-11}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less. The term "monoclonal antibody" means an antibody that is derived from a single clone, including any eukaryotic, prokaryotic, or phage clone, and not the method by which it is produced. A monoclonal antibody composition displays a single binding specificity and affinity for a particular epitope. Monoclonal antibodies can be prepared using a wide variety of techniques known in the art including, e.g., but not limited to hybridoma, recombinant, and phage display technologies.

The term "polyclonal antibody" means a preparation of antibodies derived from at least two different antibody producing cell lines. The use of this term includes preparations of at least two antibodies that contain antibodies that specifically bind to different epitopes or regions of an antigen.

The terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In particular, a modified IGF-1/E protein can be any of the modified IGF-1/E proteins described in published PCT patent application WO2007/146689, as well as any secondarily modified (glycosylated, PEGylated, etc.) proteins thereof.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. In particular, a recombinant IGF-1/E protein can be any of the recombinant IGF-1/E proteins described in published PCT patent application WO2007/146689, as well as any secondarily modified (glycosylated, PEGylated, etc.) proteins thereof.

The terms "single chain antibodies" or "single chain. Fv (scFv)" refer to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules, known as single chain Fv (scFv). See, e.g., Bird et at, *Science* 242: 423-426 (1988); and Huston et al., *Proc. Natl. Acad. Sci. USA*. 85: 5879-5883 (1988). Such single chain antibodies are included by reference to the term "antibody" fragments, and can be prepared by recombinant techniques or enzymatic or chemical cleavage of intact antibodies.

The term "specific binding" means the contact between an antibody of the invention and an epitope (on a peptide described herein (Peptide A, Peptide B or Peptide C) or a protein containing such a peptide) with a binding affinity of at least $10^{-6}$ M. Preferred binding agents hind with affinities of at least about $10^{-7}$ M, and preferably $10^{-8}$ M to $10^{-9}$ M, $10^{-10}$ M, $10^{-11}$ M, or $10^{-12}$M.

As noted above the antibodies of the invention may be labeled. Labeled antibodies may be employed in a wick variety of assays, employing a wide variety of labels. Detection of the formation of an antibody-antigen complex between an antibody of the invention and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^3$H.

Polypeptides

The invention provides an isolated polypeptide comprising or consisting of the sequence GPTLCGAELV (SEQ ID NO:1), CPAKSAVRAQR (SEQ ID NO:5 or PAKSAVRAQR (SEQ ID NO:6). Such polypeptides are useful for raising antibodies according to the invention. The polypeptides of the invention may also form part of a larger polypeptide. For example, a polypeptide of the invention may be flanked by additional n-terminal and/or c-terminal amino acids.

In general, the polypeptides of the invention are provided in a non-naturally occurring environment, i.e. they are separated from their naturally occurring environment. In certain embodiments, the polypeptide is present in a composition that is enriched for the polypeptide as compared to a control. Polypeptides of the invention are thus preferably provided in isolated or substantially isolated form i.e. the polypeptide is present in a composition that is substantially free of other expressed polypeptides, whereby substantially free is meant that less than 75% (by weight), preferably less than 50%, and more preferably less than 10% (e.g. 5%) of the composition is made up of other expressed polypeptides.

Nucleic Acid Molecules

Another aspect of the invention pertains to nucleic acid molecules that encode the polypeptides or antibodies of the invention. The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector. Nucleic acids of the invention can be obtained using standard molecular biology techniques. For antibodies expressed by hybridomas such as those described herein, cDNAs encoding the light and heavy chains of the antibody made by the hybridoma can be obtained by standard PCR amplification or cDNA cloning techniques.

Generation of Transfectomas Producing Monoclonal Antibodies

Once a nucleic acid encoding an antibody of the invention has been obtained, the antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., cDNA cloning using a hybridoma that expresses the antibody of interest) and the DNAs can be inserted into expression vectors such that the genes are operatively linked to transcriptional and translational control sequences. In this context the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the sector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely them prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621), NSO myeloma cells, COS cells and SP2 cells. In particular, for use with NSO myeloma cells, another expression system is the GS gene expression system shown in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Diagnostic Methods/Methods of Treatment

As noted above, the antibodies of the invention may be used in various assays to determine the concentration of modified IGF-1/E in a sample.

Thus the invention provides a method of determining the level of modified IGF-1/E protein in a patient, comprising the steps of:
(i) obtaining a blood sample from a patient who has been administered with said modified IGF-1/E, and
(ii) detecting the modified IGF-1/E in said sample using an antibody of the invention.

The level of modified IGF-1/E can be quantified by using standard techniques, such as by setting up calibration curves using known amounts of the modified IGF-1/E and comparing the results obtained with the test samples against the results obtained using the calibration markers (see, e.g. the examples).

Being able to determine the level of modified IGF-1/E protein in a patient also allows a physician to determine an appropriate dose in order to achieve a therapeutic effect. Thus the invention also provides a method of maintaining an optimal dose of modified IGF-1/E in a patient in need thereof, comprising:
(i) obtaining a blood sample from a patient who has been administered with said modified IGF-1/E,
(ii) detecting the modified IGF-1/E in said sample using an antibody of the invention, and
(iii) where the level of modified IGF-1/E in the patient blood sample is below a pre-determined level, administering a further dose of said modified IGF-1/E to said patient.

Note that in certain instances, a blood sample may already have been obtained from a patient. Thus the invention provides a method of determining the level of modified IGF-1/E protein in a patient, comprising the step of detecting the modified IGF-1/E in a blood sample obtained from a patient using an antibody of the invention.

The invention also provides a method of maintaining an optimal dose of modified IGF-1/E in a patient in need thereof, comprising:
(i) detecting modified IGF-1/E in a blood sample from a patient who has been administered a modified IGF-1/E using an antibody of the invention, and
(ii) where the level of modified IGF-1/E in the patient blood sample is below a pre-determined level, administering a further dose of said modified IGF-1/E to said patient.

The invention also allows the monitoring of the production of modified IGF-1/E. Thus a sample may be obtained from the production plant and probed with an antibody of the invention to confirm that the correct form of modified IGF-1/E, is being produced.

The invention also provides a method of treating a patient who is suffering from a muscle disorder comprising:

(i) determining, the serum concentration of modified IGF-1/E in a blood sample obtained from a patient who has previously been administered a modified IGF-1/E using an antibody according to the present invention; and (ii) administering more modified IGF-1/E to the patient if the serum concentration of hIGF-1/Ea 3mut is below a pre-determined optimum level.

In the embodiments described above, the modified IGF-1/E may be hIGF-1/Ea 3mut, or one described in WO2007/146689. For example, the modified IGF-1/E may be that described in example 1 of WO2007/146689 (referred to as SEQ ID NO:8 therein and modified IGF-1E No. 1 herein), or that described in example 45 of WO2007/146689 (referred to as SEQ ID NO:53 therein and modified IGF-1/E No. 2 herein).

Protein Purification

As noted above, the antibodies of the invention may also be used for commercial scale purification of modified IGF-1/E (i.e. a pharmaceutical used to treat muscle atrophy). For example, the antibodies of the invention may be used in affinity chromatography to purify modified IGF-1/E.

Purification of recombinant polypeptides is well known in the art and includes affinity chromatography purification techniques and the like (see generally Scopes, *Protein Purification* (Springer-Verlag, N.Y., 1982). See also, Bailon et al., *An Overview of Affinity Chromatography*, Humana Press (2000)). Affinity chromatography methods (such as membrane-based affinity technology) for commercial scale purification of biotherapeutic proteins are known in the art. See, Brandt et al., *Bio/Technology* 6: 779-782 (1988).

Preferably the modified. IGF-1/E purified by such methods may be hIGF-1/Ea 3mut, or one described in WO2007/146689. For example, the modified IGF-1/E may be that described in example 1 of WO2007/146689 (referred to as SEQ ID NO:8 therein and modified IGF-1E No. 1 herein), or that described in example 4 of WO2007/146689 (referred to as SEQ ID NO:53 therein and modified IGF-1/E No. 2 herein).

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and the claims. Generally, enzymatic reactions and purification steps are performed according to the manufacturer's specifications. The techniques and procedures are generally performed according to conventional methods in the art and various general references. See generally, Sambrook et al., *Molecular Cloning: A Laboratory Manual, 2d Edition* (Cold Spring Harbor Laboratory Press, Cold Spring Harbor, N.Y., 1989), which are provided throughout this document.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims along with the full scope of equivalents to which such claims are entitled.

BRIEF DESCRIPTION OF THE DRAWINGS

FIG. 1 is an amino acid sequence alignment of hIGF-1, hIGF-1/Ea wt, hIGF-1/Ea 3mut, and hIGF-2 (SEQ ID NOs: 8, 9, 10 and 11). Amino acid differences between hIGF-1/E wt and hIGF-1/E 3mut are highlighted in bold. Dashes in the sequences indicate missing residues. Peptides from hIGF-1/Ea 3mut that were selected as antigens for animal immunizations described below are underlined.

EXAMPLES

Antibodies Raised to Peptide A

Two monoclonal antibodies were generated by mouse immunizations with Peptide A, GPTLCGAELV (aa 1-10 of IGF-1/E 3mut) (SEQ ID NO:1) (see TABLE 1). The epitope recognized by QC1 and QC2 differs from wild type hIGF-1 and mIGF-1 sequence GPETLCGAELV (SEQ ID NO:2) in only one amino acid. This peptide was selected for animal immunizations, even though protein structure analysis with Biobench and Abie Pro 3.0 suggested that it has low surface probability and low antigenic index.

| | | |
|---|---|---|
| GP-TLCGAELV | hIGF-1/E 3mut | (SEQ ID NO: 1) |
| GP TLCGAELV | | (SEQ ID NO: 12) |
| GPETLCGAELV | hIGF-1/E wt, hIGF-1, mIGF-1 | (SEQ ID NO: 2) |

Hybridomas were screened with (1) recombinant hIGF-1/E 3mut (for positive clones); (2) recombinant hIGF-1/E wt protein (for negative clones); (3) recombinant hIGF-2 (for negative clones), and (4) recombinant mIGF-2 protein (for negative clones).

Figure 2:
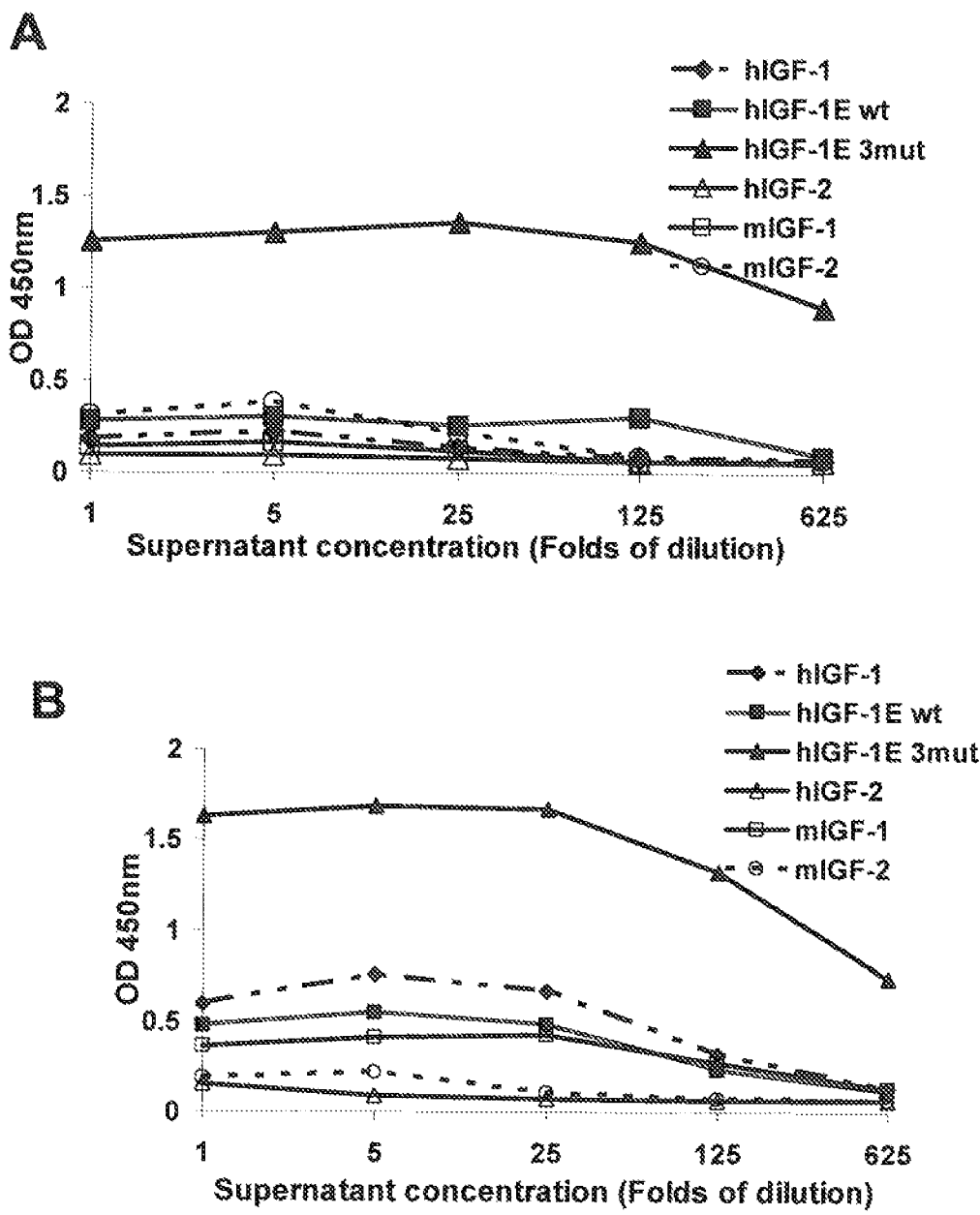
FIG. 2 is a set of charts showing the activity of the hIGF-1/E 3mut-specific mouse monoclonal antibodies generated from Peptide A immunization. Cell culture supernatants were collected from hybridoma clone QC1 (A) and QC2 (B) and diluted into microtiter wells coated with hIGF-1, hIGF-1/Ea wt, hIGF-1/Ea 3mut, hIGF-2, mIGF-1 or mIGF-2. Plate-bound antibody was detected by horse radish peroxidase-conjugated polyclonal goat anti-mouse IgG antibodies.

The antiserum titers after 3 immunizations with Peptide A-KLH conjugate from 5 mice ranged from 1:500 to 1:16,000, as determined by ELISA with hIGF-1/E 3mut. About 1,000 hybridomas were generated from mouse #3, the best responder, and 4 of them were found to be strongly reactive with hIGF-1/E 3mut but not or only weakly reactive with hIGF-1/E wt, hIGF-1, hIGF-2, mIGF-1, and mIGF-2. All 4 hIGF-1/E 3mut-reactive hybridomas were subject to subcloning, and two final subclones, QC1 (7B9C6) and QC2 (8B7A2), each derived from an independent hybridoma. Were selected and confirmed by ELISA to produce monoclonal antibody that are specific for hIGF-1/E 3mut (FIG. 2, TABLE 1).

The two mAbs, QC1 (7B9C6) and QC2 (8B7A2), are highly specific for hIGF-1/E 3mut and can be used as an immunosorbent agent (capture antibody) in a sandwich ELISA to quantify the modified recombinant human IGF-1/E peptides in pre-clinical and clinical samples. Hybridomas expressing the two mAbs QC1 (7B9C6) and QC2 (8B7A2) are deposited at DSMZ under accession numbers and, respectively.

Antibodies Raised to Peptide B

Two monoclonal antibodies were generated from mouse immunizations with Peptide B, CGDRGFYFN-KPTGYGSS (aa 17-33 of hIGF-1/E 3mut) (SEQ ID NO:3) (see TABLE 1). This peptide was selected because it has high surface probability and high antigenic index. However, hIGF-1 and hIGF-1/E 3mut have identical sequences in this region. Thus, antibodies generated against this peptide recognize all of the following proteins: hIGF-1, hIGF-1/E wt, and hIGF-1/E 3mut. In addition, mIGF-1 and hIGF-1 exhibit only one amino acid difference in this region.

```
CGDRGFYFNKPTGYGSS  hIGF-1/E 3mut,    (SEQ ID NO: 3)
                   hIGF-1, hIGF-1/E
                   wt

CG RGFYFNKPTGYGSS                    (SEQ ID NO: 13)

CGPRGFYFNKPTGYGSS  mIGF-1            (SEQ ID NO: 4)
```

Hybridomas were screened with (1) recombinant hIGF-1/E 3mut (for positive clones); (2) recombinant hIGF-2 (for negative clones); (3) recombinant mIGF-1 (for negative clones); and (4) recombinant mIGF-2 protein (for negative clones).

Figure 3:
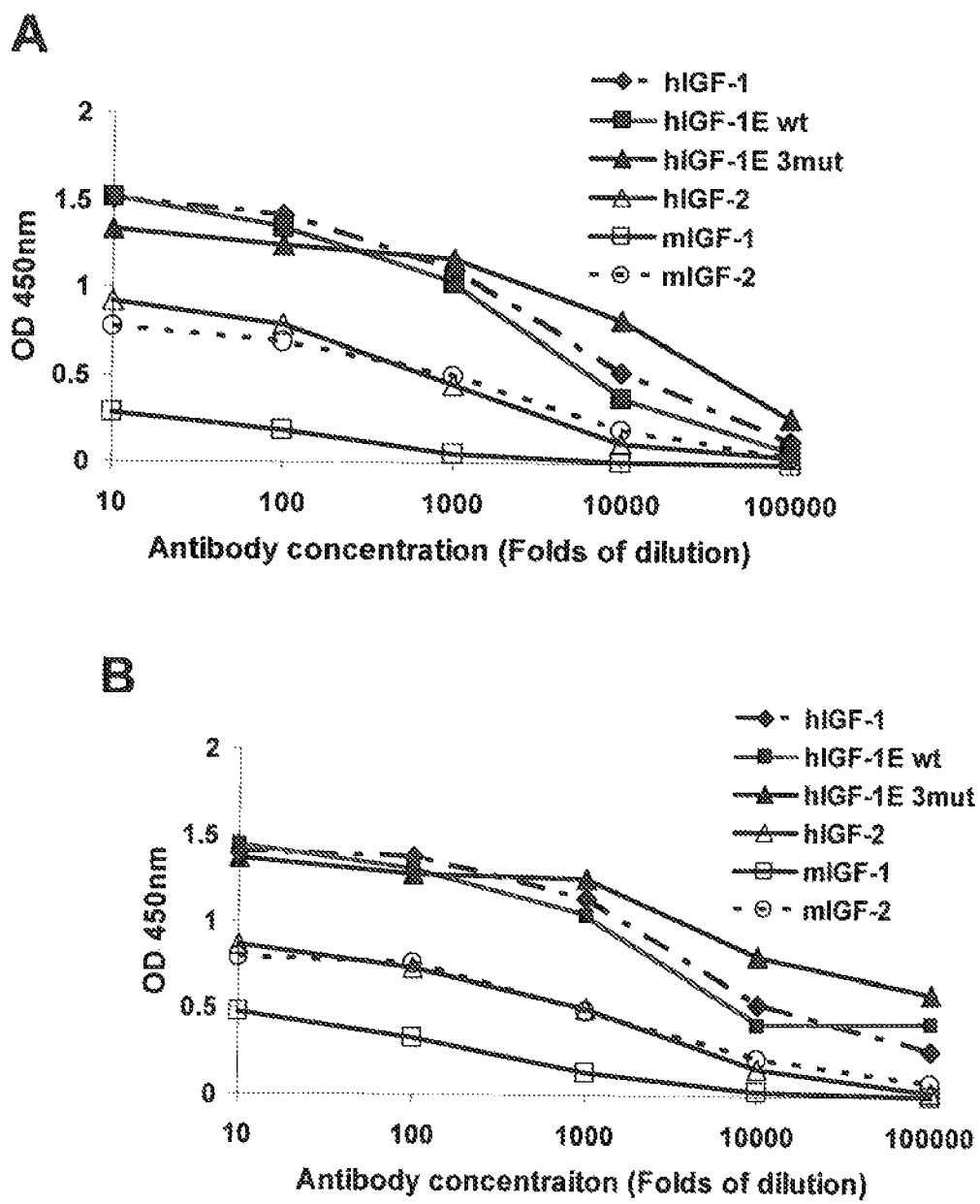
FIG. 3 is a set of charts showing the activity of the hIGF-1/E 3mut-reactive mouse monoclonal antibodies generated from Peptide B immunization. Monoclonal antibody was produced and purified from hybridoma clone BP1 (A, mg/ml) and BP2 (B, mg/ml) and diluted 1:10-1:100,000 into microtiter wells coated with hIGF-1, hIGF-1/E wt, hIGF-1/E 3mut, hIGF-2, mIGF-1 or mIGF-2. Plate-bound antibody was detected by horse radish peroxidase-conjugated polyclonal goat anti-mouse IgG antibodies.

Mouse immune responses to Peptide B were strong. The antiserum liters after 4 immunizations with Peptide B-KLH conjugate from 5 mice ranged from 1:1,000 to >1:32,000. About 1,000 hybridomas were generated from mouse #5, the best responder, and 21 of them were found to be strongly reactive with hIGF-1, hIGF-1/E wt, and hIGF-1/E 3 mut and weakly reactive with hIGF-2, mIGF-1 and mIGF-. All 13 hybridomas were subject to subcloning. Two final subclones, BP1 (2F11 D8) and BP2 (3C5D10), each derived from an independent hybridoma, were selected and confirmed to produce monoclonal antibody that bind to hIGF-1, hIGF-1/E wt and hIGF-1/E 3mut (FIG. 3, TABLE 1).

The two mAbs, BP1 (2F11D8) and BP2 (3C5D10), recognize both hIGF-1 and hIGF-1/E 3mut and cross-react with hIGF-2 and mIGF-1 and mIGF-2. Nevertheless, these mAbs might be useful for IGF-1 studies.

Antibodies Raised to Peptide C

Three monoclonal antibodies were generated from mouse immunizations with Peptide C, CPAKSAVRAQR (aa 65-74 of hIGF-1/E 3mut, plus an N-terminal C for conjugation) (SEQ ID NO:5) (see TABLE 1). This peptide of hIGF-1/E 3mut was selected because of its high surface probability and antigenic index. It spans the junctional region between mature hIGF-1 and the mutant E peptide.

```
PAKSA--VRAQR   hIGF-1/E 3mut    (SEQ ID NO: 6)

P  K+A +RAQR                    (SEQ ID NO: 14)

PTKAARSIRAQR   mIGF-1           (SEQ ID NO: 7)
```

Hybridomas were screened with (1) recombinant hIGF-1/E 3mut (for positive clones); (2) recombinant hIGF-1 (for negative clones); (3) recombinant hIGF-1/E wt (for negative clones); (4) recombinant mIGF-1 (for negative clones); and (5) recombinant mIGF-2 protein (for negative clones).

The antiserum titers after 4 immunizations with Peptide A-KLH conjugate from 5 mice ranged from 1:400 to 1:3,200. About 1,000 hybridomas were generated from mouse #4, the best responder, and 188 of them were found to be reactive with hIGF-1/E 3mut but not with hIGF-1 in standard ELISA. Of the 188 hybridomas, 20 were subject to subcloning. Three final subclones, QQ2 (2C10B7), QQ5 (6H6G11) and QQ6 (7B1H12), each derived from an independent hybridoma, were selected and confirmed to produce monoclonal antibody that recognize hIGF-1/E 3mut but not hIGF-1 (FIG. 4. TABLE 1). However, these mAbs cross-react with hIGF-1/E wt.

The epitope recognized by QQ2, QQ5 and QQ6 is PAK-SAVRAQR (aa 65-74). (SEQ ID NO: 6). These three mAbs, QQ2 (2C10B7), QQ5 (6H6G11) and QQ6 (7B1H12), recognize hIGF-1/E 3mut, cross-react with hIGF-1/E wt, but do not bind hIGF-1. Each of these mAbs could be used as an immunosorbent agent (capture antibody) in sandwich ELISA to quantify various modified recombinant human IGF-1/E peptides. Hybridomas expressing the three mAbs, QQ2 (2C10B7), QQ5 (6H6G11) and QQ6 (7B1H12) are deposited at DSMZ under accession numbers, and, respectively.

TABLE 1

Results Summary

| Epitope | Clone ID | hIGF-1/E 3mut | hIGF-1/E wt | hIGF-1 | hIGF-2 | mIGF-1 | mIGF-2 | mAb Isotype |
|---|---|---|---|---|---|---|---|---|
| Peptide A (aa 1-10) | QC1 (7B9C6) | + | − | − | − | − | − | IgG1 |
|  | QC2 (8B7A2) | + | − | − | − | − | − | IgG2a |
| Peptide B (aa 17-33) | BP1 (2F11D8) | + | + | + | +/− | +/− | +/− | IgG2a |

TABLE 1-continued

Results Summary

| Epitope | Clone ID | hIGF-1/E 3mut | hIGF-1/E wt | hIGF-1 | hIGF-2 | mIGF-1 | mIGF-2 | mAb Isotype |
|---|---|---|---|---|---|---|---|---|
| | BP2 (3C5D10) | + | + | + | +/− | +/− | +/− | IgG2a |
| Peptide C (aa 65-74) | QQ2 (2C10B7) | + | +/− | − | − | − | − | IgG1 |
| | QQ5 (6H6G11) | + | +/− | − | − | − | − | IgG1 |
| | QQ6 (7B1H12) | + | +/− | − | − | − | − | IgG1 |

Methods of Making the Antibodies of the Invention
General Methods of Making Antibodies.

Many methods of making polyclonal and monoclonal antibodies to a defined antigen (such as Peptide A, Peptide B or Peptide C) are known in the art. See, Harlow & Lane, *Antibodies, A Laboratory Manual* (Cold Spring Harbor Publications, New York, 1988) and the other references cited above.
Animal Immunizations, Hybridoma Screening, and mAB Production.

Groups of 5 BALB/c mice were immunized with each of the selected peptides conjugated to KLH. Hybridomas were screened by standard ELISA with (1) recombinant hIGF-1/E 3mut; (2) recombinant hIGF-1/E wt; (3) recombinant hIGF-1; (4) recombinant hIGF-2; (5) recombinant mIGF-1; and/or (6) recombinant mIGF-2, and hybridomas with desired specificity were selected for three rounds of subcloning and re-screening. Monoclonal antibodies were purified from cell culture supernatants of final selected hybridomas using a Protein A affinity column.

Three antigen peptides (Peptide A, Peptide B and Peptide C) were chemically synthesized and HPLC purified at GL Biochem (Shanghai) Ltd., Shanghai, China. Peptide purity was determined by mass spectrometry analysis to be immuno-grade (about 85%). These peptides contained a C residue and were conjugated to maleimide activated KM with a kit purchased from Pierce (Cat. No. 77605).

Figure 4:
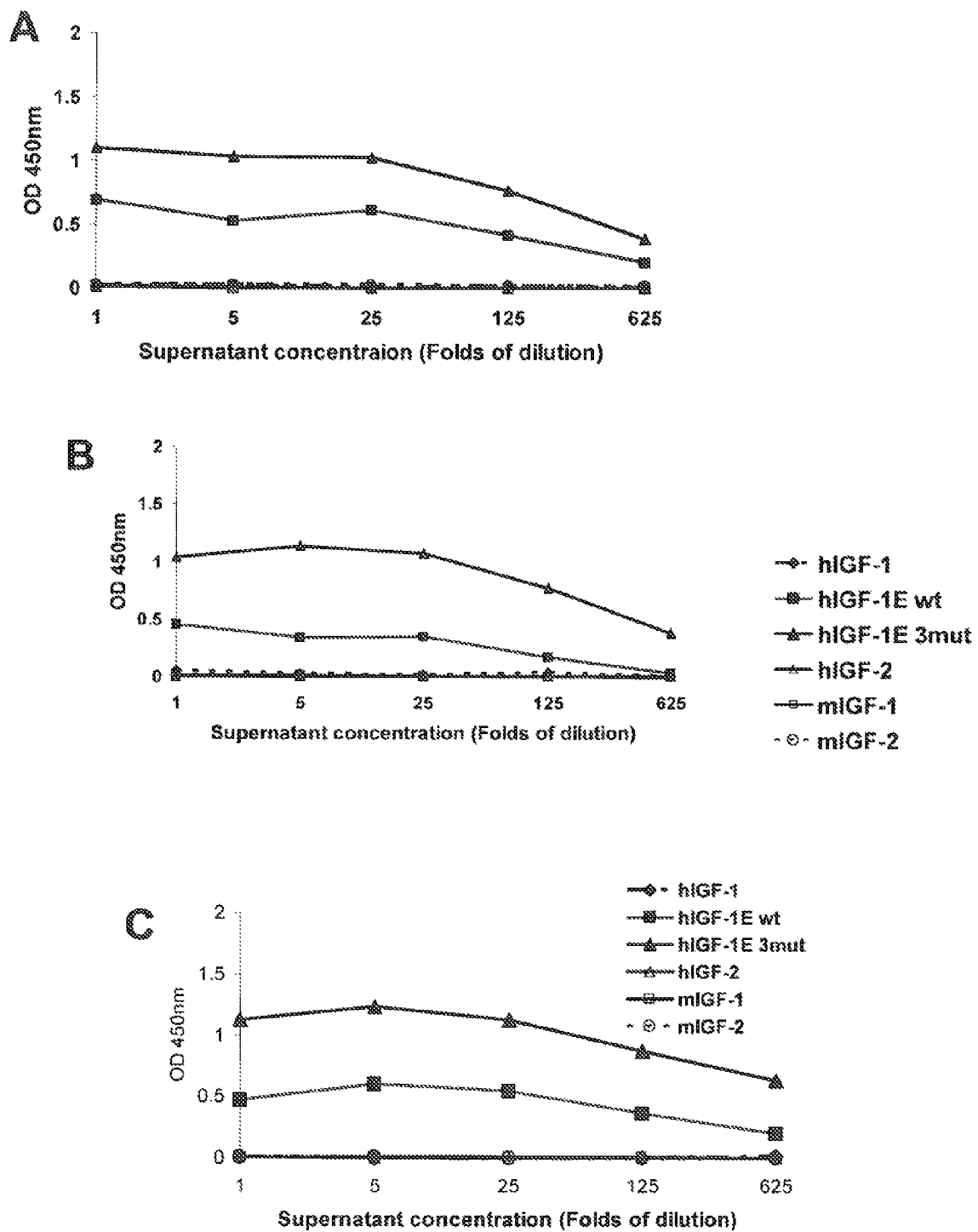
FIG. 4 is a set of charts showing the activity of the hIGF-1/E 3mut-specific mouse monoclonal antibodies generated from Peptide C immunization. Cell culture supernatants were collected from hybridoma clone QQ2 (A), QQ5 (B), and QQ6 (C) and diluted into microtiter wells coated with hIGF-1, hIGF-1/E wt, hIGF-1/E 3mut, hIGF-2, mIGF-1 or mIGF-2. Plate-bound antibody was detected by horse radish peroxidase-conjugated polyclonal goat anti-mouse IgG antibodies.

BALB/c mice at 6-8 weeks of age were used to generate antibodies. To elicit immune responses, groups of 5 mice were administered by subcutaneous injection of 50 µg of each of the three antigen peptide-KLH conjugates in CFA (for first injection) and 25 µg of each antigen in IFA (for second & third injections). Final boost immunization with 25 µg of antigen was performed by intraperitoneal injection without the use of any adjuvant. The immunization schedules were as follow:

Day 0: Pre-immunization bleed; first antigen injection
Day 26: Second antigen injection
Day 52: Third antigen injection
Day 63: Test bleed; antiserum titer ELISA
Day 69: Final boost injection
Day 73: Splenectomy Development of antigen-specific antibodies after immunizations was examined by ELISA. Nunc-Immuno microtiter plates were coated with 1 µg/ml of hIGF-1/E 3mut, hIGF-1/E wt, hIGF-1, hIGF-2, mIGF-1 or mIGF-2 in sodium carbonate-bicarbonate buffer (Pierce, Cat. No. 28382), incubated with serially diluted pre-immune and antiserum and/or hybridoma supernatant samples, and antigen-bound mouse IgG was detected with horse radish peroxidase-conjugated polyclonal goat anti-mouse IgG antibodies (Sigma, Cat. No A0168) followed by color development with BM blue PO-substrate (Roche Diagnostics, Cat. No. 1.484.281). The microtiter plates were read at 450 nm after peroxidase reaction was stopped with 2.0 M $H_2SO_4$, and ELISA data was analyzed with the software SoftMax Pro v5.2 (Molecular Devices). Results are shown in FIGS. 2-4.

Hybridomas were generated by fusing splenocytes isolated from immunized mice with the nonsecreting myeloma Sp2/0-Ag14 cells using standard procedures. ELISA assays were performed to identify hybridomas specific for the hIGF-1/E 3mut peptides.

Selected hybridomas were adapted into serum-free growth medium (Sigma, Cat. No. 24621C-500). Monoclonal antibody was purified from hybridoma supernatant by Protein A affinity column according to standard procedures and exchanged into PBS through dialysis. The isotype of purified antibodies was determined with a mouse IgG isotyping kit purchased from Southern Biotech (Cat. No. 5300-05).

Antigen-specific hybridomas were subject to three rounds of subcloning by limiting dilution (and re-screening by ELISA).

Results for antibodies generated by immunization with Peptide A, Peptide B and Peptide C are described above.
Methods of Using the Antibodies of the Invention
Immunoassays to Detect Modified IGF-1/E in a Sample.

The invention provides diagnostic assays for determining a modified IGF-1/E, protein in a biological sample (e.g., blood, serum, cells, tissue) or from individual to whom the IGF-1/E protein has been administered. Diagnostic assays, such as competitive assays rely on the ability of a labeled analogue (the "tracer") to compete with the test sample analyte for a limited number of binding sites on a common binding partner. The binding partner generally is insolubilized before or after the competition and then the tracer and analyte hound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called Enzyme-Linked ImmunoSorbent Assay (ELISA) systems when enzymes are used as the detectable markers. Such an assay, particularly in the form of an ELISA test has considerable applications in the clinical environment and in routine blood screening. See, Harlow & Lane, *Antibodies, A Laboratory Manual* (Cold Spring Harbor Publications, New York, 1988) for a description of immunoassay formats and conditions.

The immunoassays of the invention are useful in the field of predictive medicine in which diagnostic assays, prognostic assays, pharmacogenomics, and monitoring clinical trials are used for prognostic (predictive) purposes.

Sandwich ELISA Assays Using Monoclonal Antibodies of the Invention.

Figure 5:
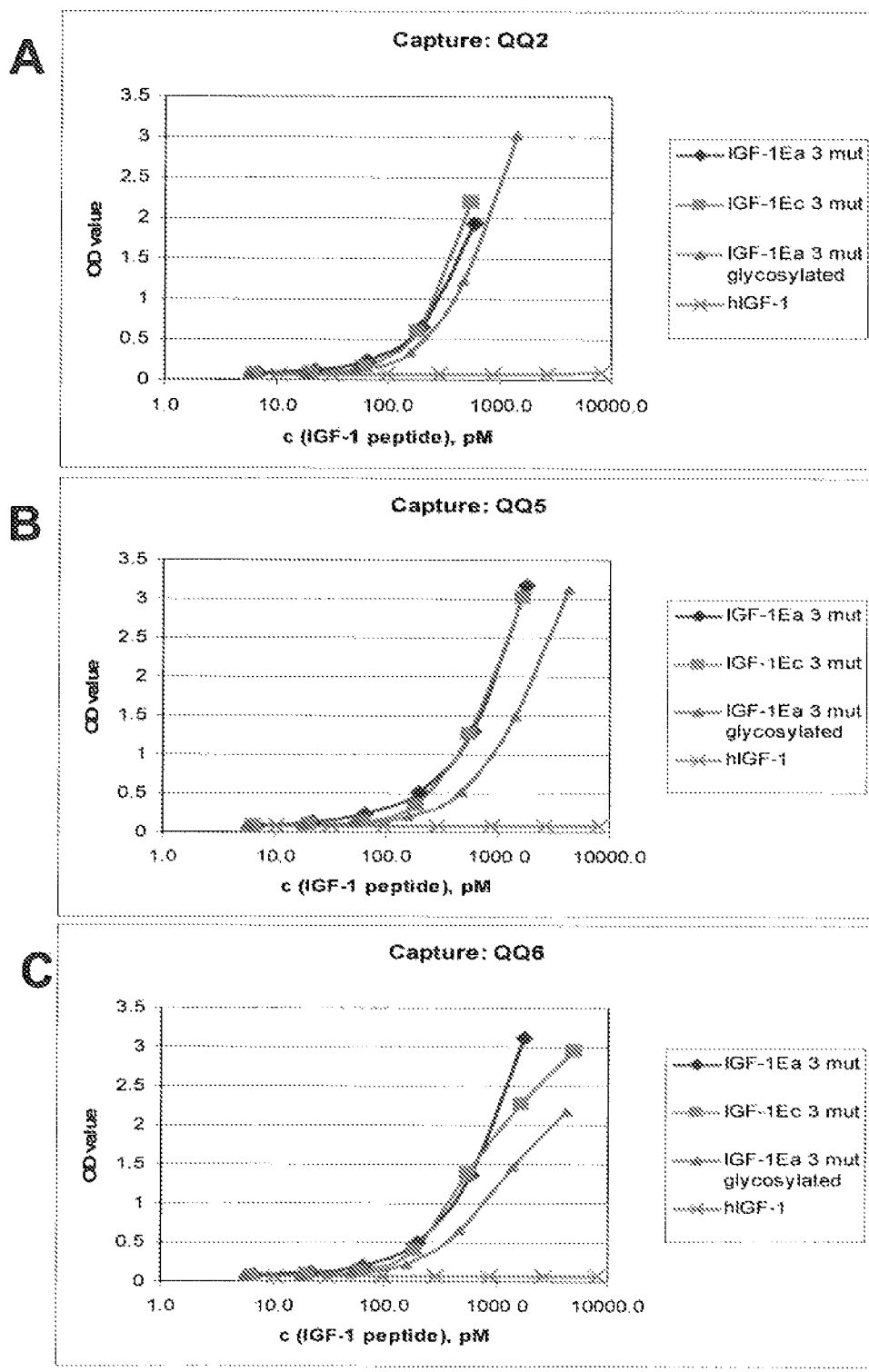
FIG. 5 is a set of charts showing the sandwich ELISA analysis of monoclonal antibodies generated from Peptide C immunization. Different concentrations of hIGF-1/Ea 3mut, hIGF-1/Ec 3mut, glycosylated hIGF-1/Ea 3mut, and hIGF-1 peptides were added to microtiter plates coated with QQ2 (A), QQ5 (B), or QQ6(C). The plate-bound IGF-1 peptides were detected with a horse radish peroxidase-conjugated monoclonal mouse anti-hIGF-1 antibody.

Each of the three mAbs generated against peptide C, QQ2, QQ5, and QQ6, was used as capture antibody and a commercially available IGF-1 mAb was used as detection reagent, were also performed to examine the specificity of QQ2, QQ5 and QQ6. As shown in FIG. 5, all three mAbs bind hIGF-1/Ea 3mut, hIGF-1/Ec 3mut and glycosylated hIGF-1/Ea 3mut, but not hIGF-1 peptide. There was no binding of either QQ2, QQ5, or QQ6 to hIGF-1 even when the hIGF-1 concentration was as high as 10 nM (FIG. 5).

For ELISA analysis, the mean OD value obtained from serially diluted antiserum and hybridoma supernatant samples was compared with the mean OD value of similarly treated preimmune serum and cell growth medium, respectively. An antiserum or hybridoma supernatant sample is considered to be reactive with the coated antigen when its OD value was at least 2 folds higher than that of the negative control.

An "isolated" or "purified" polypeptide or biologically-active portion thereof is substantially free of cellular material or other contaminating polypeptides from the cell or tissue source from which the antibody of the invention is derived, or substantially free from chemical precursors or other chemicals when chemically synthesized. For example, an isolated IGF-1/E would be free of materials that would interfere with diagnostic or therapeutic uses of the agent. Such interfering materials may include enzymes, hormones and other proteinaceous and nonproteinaceous solutes.

Evaluation of Antibody Selectivity

The selectivity of the antibody for modified IGF-1/E compared to the wt human IGF was confirmed by administering modified IGF-1/E No. 1 or No. 2 into animals, and then recovering the modified IGF-1/E using an antibody according to the invention. If more than the original amount of modified IGF-1/E administered to the animal is recovered, than this indicates unspecific binding (i.e. binding to wt IGF).

Serum samples from 7 monkeys and 7 dogs were spiked with 80 ng/ml mutant IGF No. 1, or with 200 ng/ml mutant IGF No. 2 and serum from 6 rats was spiked with 30 ng/ml mutant IGF No. 1. The concentration of mutant IGF was analysed using antibody QQ2 for mutant IGF No. 1 or QQ5 for mutant IGF No. 2.

For both antibodies, the assay was carried out in the same way. 96 well plates were coated with 100 µl antibody (QQ2 or QQ5) at a concentration of 2.5 µg/µl and left overnight. The wells were then washed twice with 300 µl blocking buffer and four times with 300 µl wash buffer. The serum samples were diluted 1:10 with assay buffer and 100 µl of each sample were added, along with 100 µl of controls (concentration of 10-3000 ng/ml) were added to the plate. The plates were then incubated for 4 hours at worn temperature with shaking.

100 µl of a biotinylated anti-human IGF-1 was then added (concentration 75 ng/ml in assay buffer) and the plates were incubated for a further hour at RT with shaking. The plates were then washed four times as described above.

100 µl of streptavidin-HRP conjugate (100 ng/ml) was added and the plates incubated for a further 30 minutes at RT with shaking. The plates were then washed four times as described above.

100 µl TMB substrate was then added to each well and incubated for 10 minutes. 100 µl stop solution was then added and the optical density read at 450 nm within 30 minutes.

The controls were used to plot a calibration curve (not shown).

Results for Antibody QQ2

| | Spiked concentration (ng/mL) | Observed concentration (ng/mL) | % Theoretical |
|---|---|---|---|
| Monkey serum number | | | |
| 1 | 80.0 | 85.39 | 106.74 |
| 2 | 80.0 | 78.42 | 98.02 |
| 3 | 80.0 | 81.38 | 101.73 |
| 4 | 80.0 | 76.66 | 95.82 |
| 5 | 80.0 | 84.47 | 105.58 |
| 6 | 80.0 | 73.64 | 92.05 |
| 7 | 80.0 | 86.99 | 108.74 |
| Pool | 80.0 | 80.86 | 101.08 |
| Dog serum number | | | |
| 1 | 80.0 | 90.6 | 113.25 |
| 2 | 80.0 | 94.26 | 117.83 |
| 3 | 80.0 | 93.79 | 117.23 |
| 4 | 80.0 | 99.34 | 124.18 |
| 5 | 80.0 | 92.69 | 115.86 |
| 6 | 80.0 | 99.84 | 124.81 |
| 7 | 80.0 | 94.98 | 118.73 |
| Pool | 80.0 | 91.02 | 113.78 |
| Rat serum number | | | |
| 1 | 30.0 | 30.88 | 102.93 |
| 2 | 30.0 | 29.79 | 99.29 |
| 3 | 30.0 | 32.30 | 107.68 |
| 4 | 30.0 | 33.00 | 109.99 |
| 5 | 30.0 | 33.29 | 110.97 |
| 6 | 30.0 | 37.38 | 124.59 |
| Pool | 30.0 | 29.71 | 99.04 |

Results for Antibody QQ5

| | Spiked concentration (ng/mL) | Observed concentration (ng/mL) | % Theoretical |
|---|---|---|---|
| Monkey serum number | | | |
| 1 | 200.0 | 202.74 | 101.37 |
| 2 | 200.0 | 201.96 | 100.98 |
| 3 | 200.0 | 197.64 | 98.82 |
| 4 | 200.0 | 205.72 | 102.86 |
| 5 | 200.0 | 188.96 | 94.48 |
| 6 | 200.0 | 211.03 | 105.52 |
| 7 | 200.0 | 209.29 | 104.65 |
| Pool | 200.0 | 209.55 | 104.78 |
| Dog serum number | | | |
| 1 | 200.0 | 245.11 | 122.56 |
| 2 | 200.0 | 230.96 | 115.48 |
| 3 | 200.0 | 224.84 | 112.42 |
| 4 | 200.0 | 224.11 | 112.06 |
| 5 | 200.0 | 211.27 | 105.64 |
| 6 | 200.0 | 251.15 | 125.57 |
| 7 | 200.0 | 214.18 | 107.09 |
| Pool | 200.0 | 231.13 | 115.56 |

Specificity/selectivity is the ability of an analytical method to measure and differentiate the analyte in the presence of other similar and/or unrelated constituents in the samples. It is investigated by evaluating the accuracy obtained from measuring an amount of the analyte added to and recovered from the biological matrix. Target acceptance criteria for specificity/selectivity is that acceptable recovery is obtained for at least 80% of the matrices evaluated. Acceptable recovery was defined for our method as 75-125%. Since all of the investigated individual matrices were within the acceptance criteria we consider this method to be specific and selective.

The invention claimed is:

1. An isolated antibody that binds immunospecifically to the peptide GPTLCGAELV (SEQ ID NO: 1) but does not bind immunospecifically to the peptide GPETLCGAELV (SEQ ID NO: 2), wherein said isolated antibody is produced by a hybridoma deposited at DSMZ under accession number DSM ACC3028 or DSM ACC3026.

2. An isolated antibody selected from the group consisting of QC1 and QC2, wherein said isolated antibody is produced by a hybridoma deposited at DSMZ under accession number DSM ACC3028 or DSM ACC3026.

3. A hybridoma expressing an antibody, selected from the group consisting of QC1 and QC2, wherein the hybridoma is deposited at DSMZ under accession number DSM ACC3028 or DSM ACC3026.

* * * * *

SEQUENCE LISTING

<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      modified IGF-1 peptide

<400> SEQUENCE: 1

Gly Pro Thr Leu Cys Gly Ala Glu Leu Val
1               5                   10

<210> SEQ ID NO 2
<211> LENGTH: 11
<212> TYPE: PRT
<213> ORGANISM: Homo sapiens

<400> SEQUENCE: 2

Gly Pro Glu Thr Leu Cys Gly Ala Glu Leu Val
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      modified IGF-1 peptide

<400> SEQUENCE: 3

Cys Gly Asp Arg Gly Phe Tyr Phe Asn Lys Pro Thr Gly Tyr Gly Ser
1               5                   10                  15

Ser

<210> SEQ ID NO 4
<211> LENGTH: 17
<212> TYPE: PRT
<213> ORGANISM: Mus musculus

<400> SEQUENCE: 4

Cys Gly Pro Arg Gly Phe Tyr Phe Asn Lys Pro Thr Gly Tyr Gly Ser
1               5                   10                  15

Ser

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      modified IGF-1 peptide

<400> SEQUENCE: 5

Cys Pro Ala Lys Ser Ala Val Arg Ala Gln Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      modified IGF-1 peptide

```
<400> SEQUENCE: 6

Pro Ala Lys Ser Ala Val Arg Ala Gln Arg
1               5                   10

<210> SEQ ID NO 7
<211> LENGTH: 12
<212> TYPE: PRT
<213> ORGANISM: Mus musculus

<400> SEQUENCE: 7

Pro Thr Lys Ala Ala Arg Ser Ile Arg Ala Gln Arg
1               5                   10

<210> SEQ ID NO 8
<211> LENGTH: 70
<212> TYPE: PRT
<213> ORGANISM: Homo sapiens

<400> SEQUENCE: 8

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 9
<211> LENGTH: 86
<212> TYPE: PRT
<213> ORGANISM: Homo sapiens

<400> SEQUENCE: 9

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys
                85

<210> SEQ ID NO 10
<211> LENGTH: 83
<212> TYPE: PRT
<213> ORGANISM: Artificial Sequence
<220> FEATURE:
<223> OTHER INFORMATION: Description of Artificial Sequence: Synthetic
      hIGF-1/Ea triple mutant polypeptide

<400> SEQUENCE: 10

Gly Pro Thr Leu Cys Gly Ala Glu Leu Val Asp Ala Leu Gln Phe Val
1               5                   10                  15
```

```
Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
        35                  40                  45

Arg Ser Cys Asp Leu Arg Leu Glu Met Tyr Cys Ala Pro Leu Lys
 50                  55                  60

Pro Ala Lys Ser Ala Val Arg Ala Gln Arg His Thr Asp Met Pro Lys
 65                  70                  75                  80

Thr Gln Lys

<210> SEQ ID NO 11
<211> LENGTH: 83
<212> TYPE: PRT
<213> ORGANISM: Homo sapiens

<400> SEQUENCE: 11

Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
 50                  55                  60

Lys Ser Ala Arg Asp Val Ser Thr Pro Pro Thr Val Leu Pro Asp Asn
 65                  70                  75                  80

Phe Pro Arg

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present

<400> SEQUENCE: 12

Gly Pro Glu Thr Leu Cys Gly Ala Glu Leu Val
 1               5                  10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Pro

<400> SEQUENCE: 13

Cys Gly Xaa Arg Gly Phe Tyr Phe Asn Lys Pro Thr Gly Tyr Gly Ser
 1               5                  10                  15

Ser

<210> SEQ ID NO 14
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Thr
<220> FEATURE:
<221> NAME/KEY: MOD_RES
<222> LOCATION: (4)..(4)
<223> OTHER INFORMATION: Ser or Ala
<220> FEATURE:
<221> NAME/KEY: MOD_RES
<222> LOCATION: (6)..(7)
<223> OTHER INFORMATION: May or may not be present
<220> FEATURE:
<221> NAME/KEY: MOD_RES
<222> LOCATION: (8)..(8)
<223> OTHER INFORMATION: Val or Ile

<400> SEQUENCE: 14

Pro Xaa Lys Xaa Ala Arg Ser Xaa Arg Ala Gln Arg
1               5                   10
```